(12) United States Patent
Olsson

(10) Patent No.: US 6,889,687 B1
(45) Date of Patent: May 10, 2005

(54) INHALATOR WITH AEROSOLIZING UNIT

(75) Inventor: Thomas Olsson, Stockholm (SE)

(73) Assignee: SHL Medical AB, Nacka (SE)

( * ) Notice: Subject to any disclaimer, the term of this patent is extended or adjusted under 35 U.S.C. 154(b) by 111 days.

(21) Appl. No.: 10/129,072

(22) PCT Filed: Nov. 2, 2000

(86) PCT No.: PCT/SE00/02099

§ 371 (c)(1),
(2), (4) Date: May 2, 2002

(87) PCT Pub. No.: WO01/32247

PCT Pub. Date: May 10, 2001

(30) Foreign Application Priority Data

Nov. 2, 1999 (SE) .............................................. 9903990

(51) Int. Cl.$^7$ ............................................ A61M 11/00
(52) U.S. Cl. ............................. 128/200.14; 128/200.16; 128/200.17; 128/200.23
(58) Field of Search ..................... 128/200.14, 200.15, 128/200.16, 200.17, 200.21, 200.23

(56) References Cited

U.S. PATENT DOCUMENTS

| | | | |
|---|---|---|---|
| 3,456,644 A | 7/1969 | Thiel | |
| 3,456,646 A | 7/1969 | Phillips et al. | |
| 4,576,157 A | 3/1986 | Raghuprasad | |
| 4,664,107 A * | 5/1987 | Wass | 128/200.23 |
| 5,331,954 A * | 7/1994 | Rex et al. | 128/200.22 |
| 5,435,282 A * | 7/1995 | Haber et al. | 128/200.16 |
| 5,497,944 A * | 3/1996 | Weston et al. | 239/321 |
| 5,894,841 A | 4/1999 | Voges | |
| 6,443,146 B1 * | 9/2002 | Voges | 128/200.14 |

* cited by examiner

*Primary Examiner*—Glenn K. Dawson
*Assistant Examiner*—Darwin P Erezo
(74) *Attorney, Agent, or Firm*—Young & Thompson (57) ABSTRACT

A portable, handheld breath actuated inhalator, to aerosolize and distribute a pressurised liquid, including a breath flow path defined between an air inlet (132) and a mouthpiece (131) outlet, a container (30) for the liquid, an aerosolizing element (115) for introducing the aerosolized liquid into the breath flow path, a valve element (113) between the container and the aerosolizing means for allowing fluid communication between the container and the aerosolizing element, and an actuator to regulate the valve element. The actuator is mechanical and is energized by the flow of inhaled air.

11 Claims, 11 Drawing Sheets

INHALATOR WITH AEROSOLIZING UNIT

This application is a 371 of PCT/SE00/02099 dated Nov. 2, 2000.

TECHNICAL FIELD OF THE INVENTION

The present invention relates to a portable handheld inhalator for the administration of a pharmaceutically active substance, and more specifically to a portable handheld inhalator being actuated by the breath of the patient.

TECHNICAL BACKGROUND OF THE INVENTION

There is a general need for portable handheld inhalators. A common group of inhalators are those that deliver an aerosolized drug in a fixed unit dosage when an actuator is pressed, squeezed or pulled by the patient.

It has been found that such inhalators are not optimal in that the delivered drug is not always introduced effectively into the respiratory passages of the patient. The coordination between the inhalation and the triggering of the drug delivery is critical and introduces the risk of an untimely administration with respect to the breathing. In addition, the breathing cycle and strength differs between different patients which introduces another difficulty.

Therefore, breath actuated inhalators have been developed. Such inhalators are provided with some kind of device that is sensitive to an airflow. Thus, when the patient inhales through a mouthpiece of the device, the sensitive device triggers the distribution of the drug. The drug is delivered into the airflow, i.e. the patient's inhalation, to continue into the respiratory passages of the patient.

Such inhalators, wherein a fixed unit dosage is administered when the patient inhales, are known, for example through WO 92/09323.

However, even with such unit dosage inhalators it is possible that the pharmaceutics is not inhaled in the most effective way. Therefore, electromechanically actuated inhalators are known that monitors the inhaled air flow and opens and closes, respectively, a valve in response to the measured air flow, i.e. a continuous administration of the drug is obtained, the length of which is determined by the respective inhalation of the patient.

An example of such an inhalator is described in the U.S. Pat. No. 5,718,222. With reference to FIG. 17 of said patent, a formulation is contained in a container that is closed by a valve. When a control unit has received a signal from a flow sensor being connected to the mouthpiece of the device, thereby indicating that the patient is inhaling, an actuator opens the valve in response to a signal from the control unit. With the valve open, the formulation enters into a resonance cavity where it is excited by a vibrating electromechanical mechanism to force the formulation through a membrane. The formulation exits from the membrane in an aerosolized state to be inhaled by the patient.

In order to obtain an aerosolization with very small and well-defined droplets the membrane of the device according to U.S. Pat. No. 5,718,222 is a so called Rayleigh type membrane. The Rayleigh flow phenomena is well known within the art, and is for example described in Hydrodynamics, Horace H. Lamb, 6th edition, p. 472–475, Dover Publication, New York, 1945.

An example of a breath activated inhalator utilizing a Rayleigh type membrane is described in the patent U.S. Pat. No. 5,718,222 referred to above. According to this patent, a pressurised liquid is propelled through the membrane.

Thus, although the inhalator according to U.S. Pat. No. 5,718,222 addresses the problem of drug administration controlled by the breath of the patient, it requires an electromechanical arrangement. This is a disadvantage in many applications, where low cost and small size is desired. In addition thereto, the need for electric energy makes the device vulnerable under circumstances where new batteries or an external energy source are not obtainable.

Therefore, there still remains a need for an all-mechanic breath controlled inhalator for continuously administering a drug when the patient is inhaling above a predetermined flow rate. The term "all-mechanic" is not to be regarded as excluding electric or electronic means and parts which facilitates the use of the inhaler, such as for example electronic display means, means for electronically monitoring the inhalation quality.

SUMMARY OF THE INVENTION

It is an object of the present invention to provide a device in response to the need described above.

According to the invention, a mechanical breath actuated inhalator is provided. Due to its mechanical working, the inhalator requires no external energy source, which makes it reliable under all circumstances.

A mechanical inhalator according to the invention, such as an inhalator according to any one of the embodiments shown in the detailed description, allows the manufacturing of a reliable inhalator at a relatively low cost.

Furthermore, the present invention makes it possible to design an inhalator for "puffing" a pharmaceutics, i.e. a certain dosage of a pharmaceutics could be inhaled by several breathings in stead of inhaling the entire dosage in one single breath. For example, this allows a patient to inhale nicotine in a way that very much resembles smoking.

In addition, the inhalator could be designed to very small dimensions, thereby allowing a discrete way to inhale a pharmaceutics. In a preferred embodiment for use in anti-smoking treatment, the inhalator could be formed with a size and shape similar to a cigarette.

The present invention, as well as further scope of applicability, will become apparent from the detailed description given hereinafter. However, it should be understood that the detailed description and specific examples, while indicating preferred embodiments of the invention are given by way of illustration only. Various changes and modifications within the spirit and scope of the invention will become apparent to those skilled in the art from this detailed description.

BRIEF DESCRIPTION OF THE DRAWINGS

The present invention is described with reference to the accompanying drawings, which are given by way of illustration only and thus are not limiting the present invention, and wherein FIG. 1 is a perspective view of a first embodiment of an aerosolizing unit according to the present invention.

FIG. 2 is a perspective view of the aerosolizing unit of FIG. 2, viewed from a second position.

FIG. 3 is a perspective view of a complete inhalator according to the invention.

FIG. 4 is a cross sectional view of the inhalator according to FIG. 3.

FIG. 5 is an enlarged cross sectional view through the mouthpiece of the inhalator of FIG. 3.

It should be noted that terms related to direction, such as "upper section" or "downward direction", are used in the description for distinctive purpose and are typically related to a corresponding figure of the drawings. Thus, such terms should not be understood as limiting the scope of the invention.

DETAILED DESCRIPTION OF PREFERRED EMBODIMENTS

In an inhalator with an aerosolizing unit according to the invention a force is developed by a flow of air, i.e. the inhaled breath of the patient, said force via a mechanical actuating means acting on a valve means to open the valve as long as the flow of air is above a selected parameter, such as a flow rate or a pressure.

As long as the valve is open, a pressurised liquid such as a pharmaceutically active drug is aerosolized and delivered to the flow of air to be adminstered into the air passages of the patient. The delivery continues until the selected parameter of the air flow has decreased to a certain level under which the mechanism no longer manages to keep the valve open. Typically, the level which the air flow has to exceed to opening the valve is essentially the same as the level below which the valve closes.

The opening as well as the closing air flow level or levels is/are determined by the cooperative dimensions of the elements forming the valve means and the valve actuating means, as will be described.

A first embodiment of an aerosolizing unit 10 according to the invention for use in an inhalator is shown in FIGS. 1 to 6.

Figure 1:
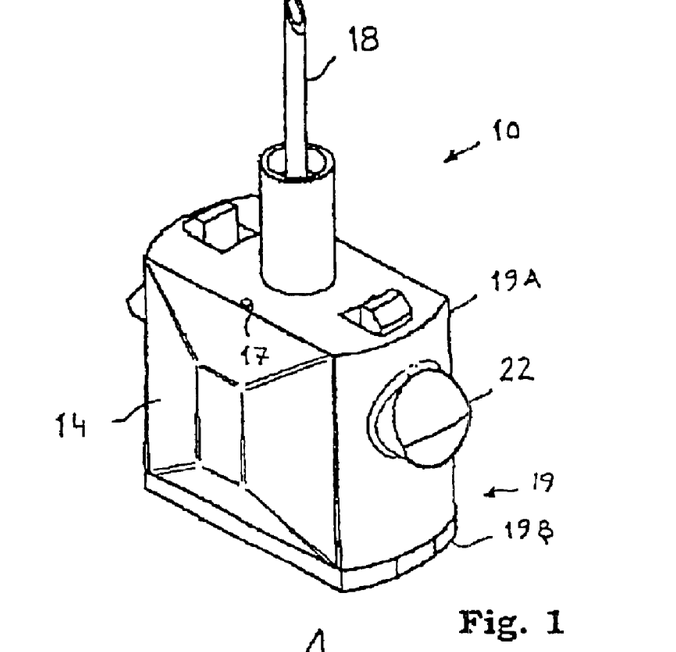

FIG. 1 shows the aerosolizing unit 10 from an angle wherein a flexible membrane 14 mounted at one side of on a body 19 is visible, as well as a generally tubular conduit, i.e. a hollow needle 18, for coupling a liquid container thereto. The body 19 consists of an upper body section 19A and a lower body section 19B.

Figure 2:
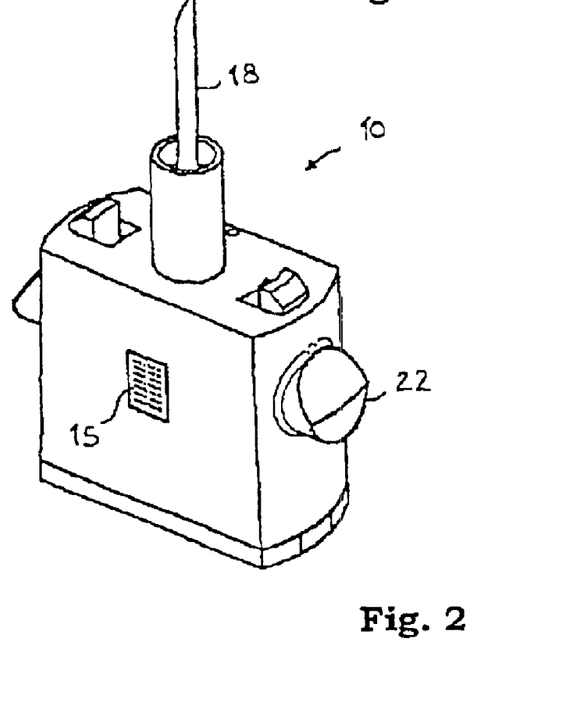

FIG. 2 shows the other side of the aerosolizing unit 10 of FIG. 1, wherein a porous membrane 15 is visible. The aerosolizing unit 10, which is adapted to be mounted in a generally tubular air conduit by means of a couple of protruding fastening means 22, will now be described in detail.

Figure 3:
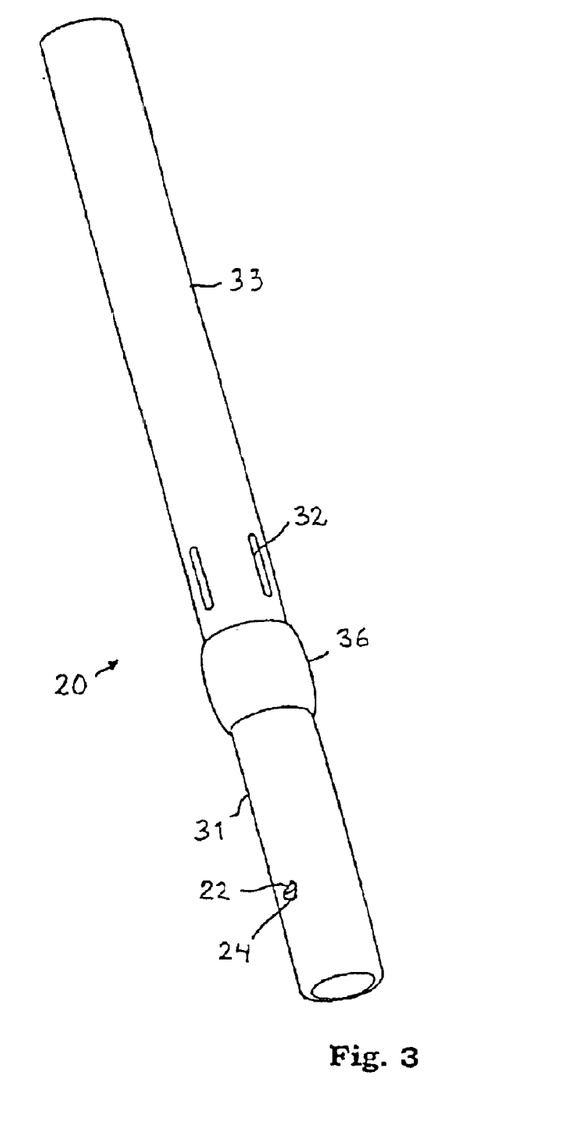

An embodiment of a complete inhalator 20 according to the invention including the aerosolizing unit 10 of FIGS. 1 and 2 is shown in the perspective view of FIG. 3. The inhalator has an upper section 33 containing a drug container (not visible in FIG. 3), a lower section forming a mouthpiece 31, and a connecting means 36 for releasably joining the upper section 33 with the mouthpiece 31. Holes 24 for receiving the fastening means 22 of the aerosolizing unit 10 are provided.

Figure 4:
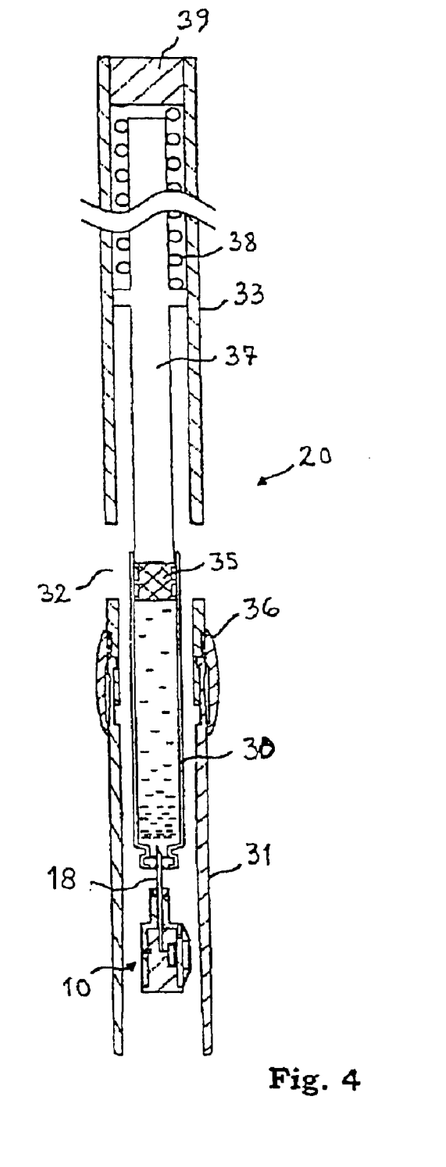

FIG. 4 shows a cross sectional view of the inhalator 20 of FIG. 3. A cartridge 30 containing the liquid to be aerosolized, i.e. typically a drug including a liquid containing a pharmaceutically active substance, is attached to the aerosolizig unit 10 via the hollow needle 18. The needle 18 is inserted through a penetrable membrane at the proximal end of the cartridge 30. At the distal end of the cartridge 30 an end wall 35 is sealingly slidable. Thus, when an external force is applied to urge the end wall 35 into the cartridge, at the same time as the outlet at the proximal is obstructed, the liquid pressure in the cartridge is increased.

The upper section 33 of the inhalator; which is attached to the mouthpiece 31 in a releasable manner using for example a thread or a bayonet fitting 36, comprises a piston 37 and a coil spring 38 being supported by an end member 39. Air inlet openings 32 are provided in the upper section 33.

When the upper inhalator section 33 and the mouthpiece section 31 are mated, the piston 37 urges the slidable wall 35 of the cartridge 30 inwards by the bias of the spring 38. The length and diameter of the piston 37 as well as the spring force of the spring 38 and its connection to the piston are adapted to provide a liquid pressure in the cartridge 30.

Figure 5:
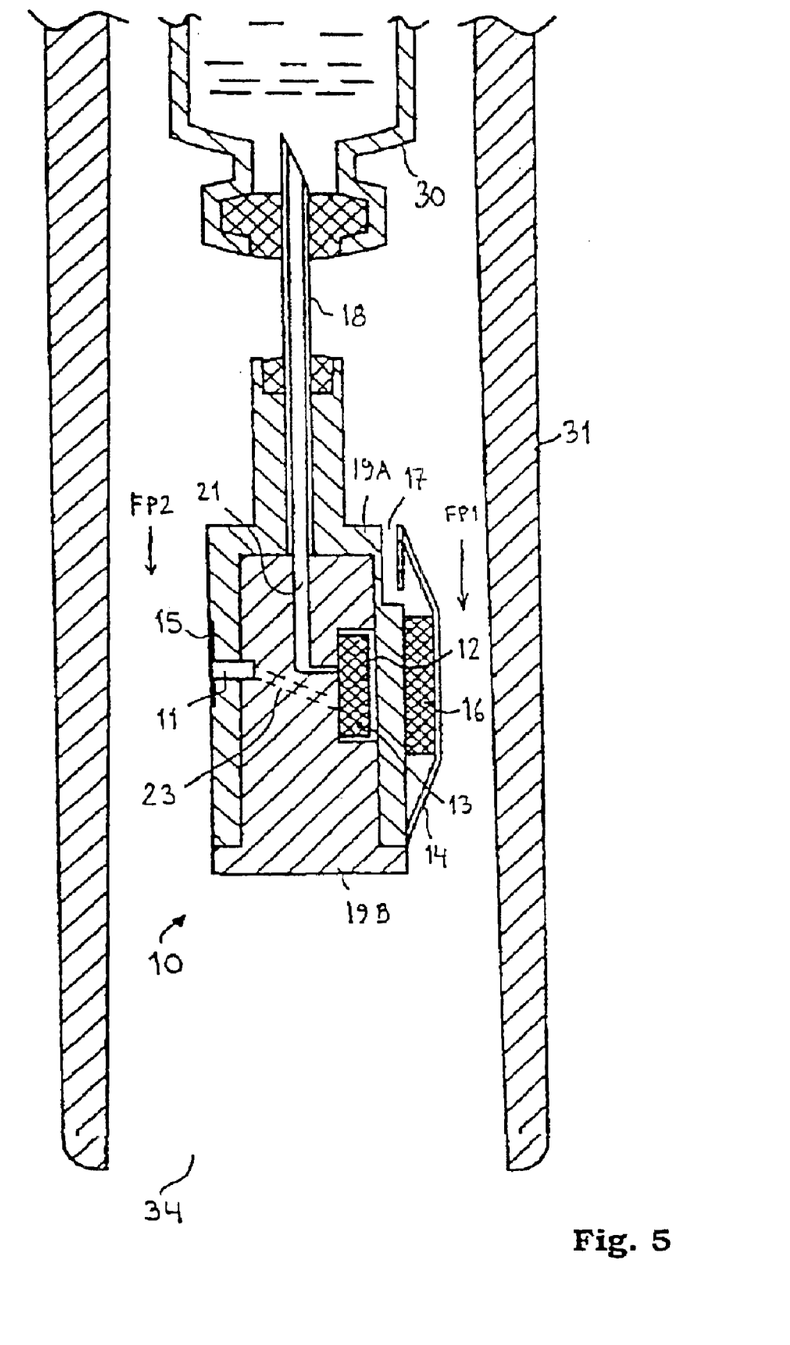

The enlarged cross sectional view of FIG. 5 shows the mouthpiece 31 and the aerosolizing unit 10 contained therein.

The inhalation of the patient creates a flow of air through a flow path extending through the inhalator, from the air inlet openings 32 to the mouthpiece outlet 34. When passing the aerosolizing unit 10 the flow of air is generally parted into a first flow path FP1 at one side of the aerosolizing unit 10 and a second flow path FP2 at the other side of aerosolizing unit 10.

As described above, the hollow needle 18 of the aerosolizing unit 10 is inserted into the pharmaceutics cartridge 30 to allow the pharmaceutics to enter into the aerosolizing unit 10 via the lumen of the needle 18. The lumen of the needle 18 is in fluid communication with an end of a channel 21. The other end of the channel 21 is sealed by a sealing member 13, thereby preventing the liquid to enter into a chamber 12 also in the case when the liquid is under pressure from the piston 37.

The sealing member 13 forms a valve means for allowing and disrupting a flow of liquid out of the channel 21. The sealing member 13 is made from a permanent magnetic material or includes such a material.

A mechanical means for actuating the sealing member 13 comprises a magnetic member 16 being attached to a flexible membrane 14 for interaction with the magnetic material of the sealing member 13. By forming the upper and lower body section from a non-magnetic material, such as a suitable polymer, the magnetic member 16 is allowed to interact with the sealing member 13.

The magnetic field strength and polarities of the sealing member 13 (first magnet) and the second magnetic member 16, respectively, are selected such that the members repel each other with a force high enough to counteract the pressure force of the pressurised channel 21 when no, or a very small, air flow is acting on the membrane.

The membrane, that is formed from a suitable flexible material such as an elastomer, is shown having a generally dome-shaped form (although other forms are possible) and its edge(s) is attached to the body of the aerosolizing unit 10. The outer surface of the membrane is disposed in a first flow path FP1 through the mouthpiece 31. The other side of the membrane 14 is also, via a channel 17, in fluid communication with the air in the mouthpiece. However, the air in the channel 17 is essentially static with respect to the air flowing in the flow path FP1.

As is shown with hidden lines (dot lines) in FIG. 5, the chamber 12 is via a channel 23 through the body 19A, 19B in communication with an outlet opening 11 at the opposite side of the aerosolizing unit 10 with respect to the membrane 14. The opening 11 is covered by the porous membrane 15 being provided with through pores of microscopic sizes. It should be noted that the microscopically small pores are not indicated in FIG. 5, although they are symbolised with dots in FIG. 2.

The membrane 15 is preferably a Rayleigh type membrane having pores with a diameter in the range of about 0.25 to 6 $\mu$m. The specific dimension and shapes of the pores should be selected to suit the specific pharmaceutical drug, for example based on directions given in the publication "Hydrodynamics" per above.

However, other types of membranes as well as nozzle arrangements could of course be used in connection with the invention to aerosolize the drug.

The porous membrane 15 is exposed to a second flow path FP2.

In use, the patient inhales through the end of the mouthpiece 31, thereby creating a flow of air from the air inlet opening 32 via the first and second flow paths FP1, FP2 and into the mouth of the patient.

According to FIG. 5, the air flow in the first flow path FP1 creates a lower pressure on the outside of the membrane 14 than on the inside of the membrane 14. Therefore an outwardly directed force is created that urges the central part of membrane 14 out from the body of the aerosolizing unit 10. Since the second magnetic member 16 is fixed to the inside of membrane 14 it follows the membrane outwards.

When the air flow across the membrane reaches a sufficient strength, i.e. a sufficient flow rate, the membrane and consequently the second magnetic member are displaced a sufficient distance from the sealing member 13 for the magnetic field strength, being approximately reciprocally proportional to the square of the distance, no longer to be strong enough to urge the sealing member 13 to seal the channel 21. Consequently, the size and the bending stiffness of the membrane should be correlated with a desired opening air flow rate to open the channel 21 at a proper flow rate to provide optimal inhalation efficiency.

Thus, when an air flow of a certain flow rate sweeps over the flexible membrane 14, it lifts the membrane to allow the channel 21 to open, and in consequence the pressurised liquid of the cartridge 30 enters the channel 12 to reach the porous membrane 15 via the channel 23 and the opening 11.

When the channel 12 is filled with pressurised liquid, and as long as the sealing element 13 is lifted above the channel 21, liquid will be forced out through the pores of the membrane 15. Outside of the porous membrane 15 Rayleigh type droplets are formed to be emitted into the airflow of the second flow path FP2. Consequently, the drug droplets are carried away by the airflow and into the patient's respiratory passages as desired.

When the airflow over the flexible membrane decreases below a closing level, which in the present embodiment is essentially the same as air flow necessary to open the valve means 13, the flexible membrane 14 returns to approach its initial position. Consequently, the magnetic force on the sealing member 13 is increased until the sealing member 13 again closes the channel 21. Substantially at that moment the output of droplets from the porous membrane 15 ceases.

The distribution of liquid according to the description above could be repeated as long as there is liquid under pressure in the channel 21.

Of course, it is possible to design the complete inhalator as a disposable inhalator, but for both economical and environmental reasons it is preferred to make the aerosolizing unit and the inhalator casing as multiple use components, while the cartridge is a disposable. Thus, when a cartridge 30 is emptied, the upper section 33 is disconnected from the mouthpiece 31 to expose the empty cartridge, which then can be replaced by a fresh cartridge.

Although the mechanical actuating means of the first embodiment has been described comprising two magnetic members repelling each other, it is of course possible to arrange them in a different way. For example, by placing the actuating means at the other side of the channel 21, in respect to the valve means 13 as seen in FIG. 5, and also change the position of the porous membrane 15, the magnetic members could be arranged to attract each other in stead.

A second embodiment of a handheld portable small size inhalator according to the present invention shall now be described with reference to FIGS. 6 to 9.

Figure 6:
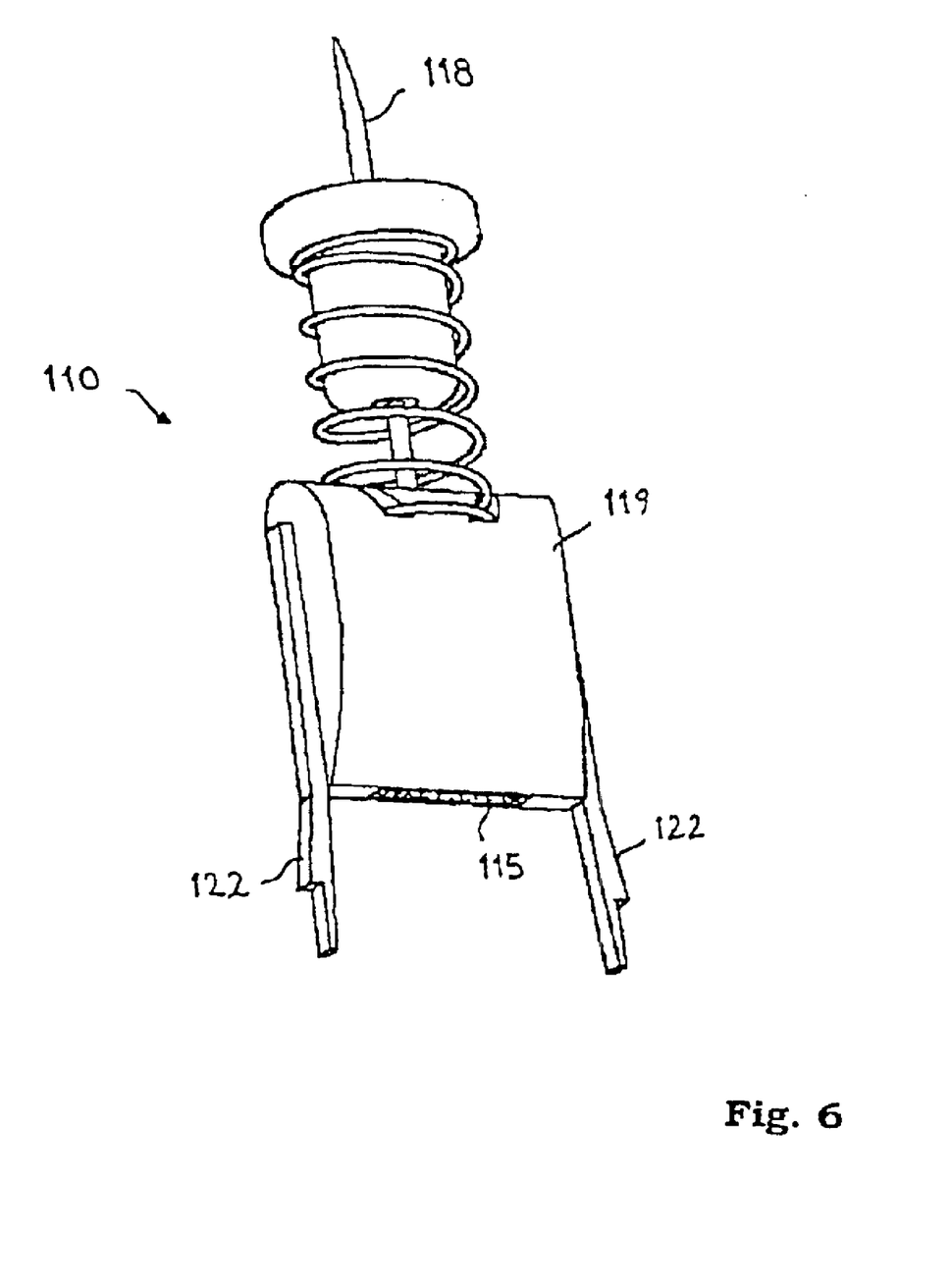
FIG. 6 is a perspective view of a second embodiment of an aerosolizing unit according to the present invention.

In the perspective view of FIG. 6 is shown a second embodiment of an aerosolizing unit 110 to be attached to the mouthpiece of the inhalator by fastening means 122. A generally tubular conduit, i.e. a needle 118 for coupling to the drug cartridge is attached to the body 119 of the aerosolizing unit 110. A porous membrane 115 for delivering the drug in an aerosolized form is visible at the end of the body 119.

Figure 7:
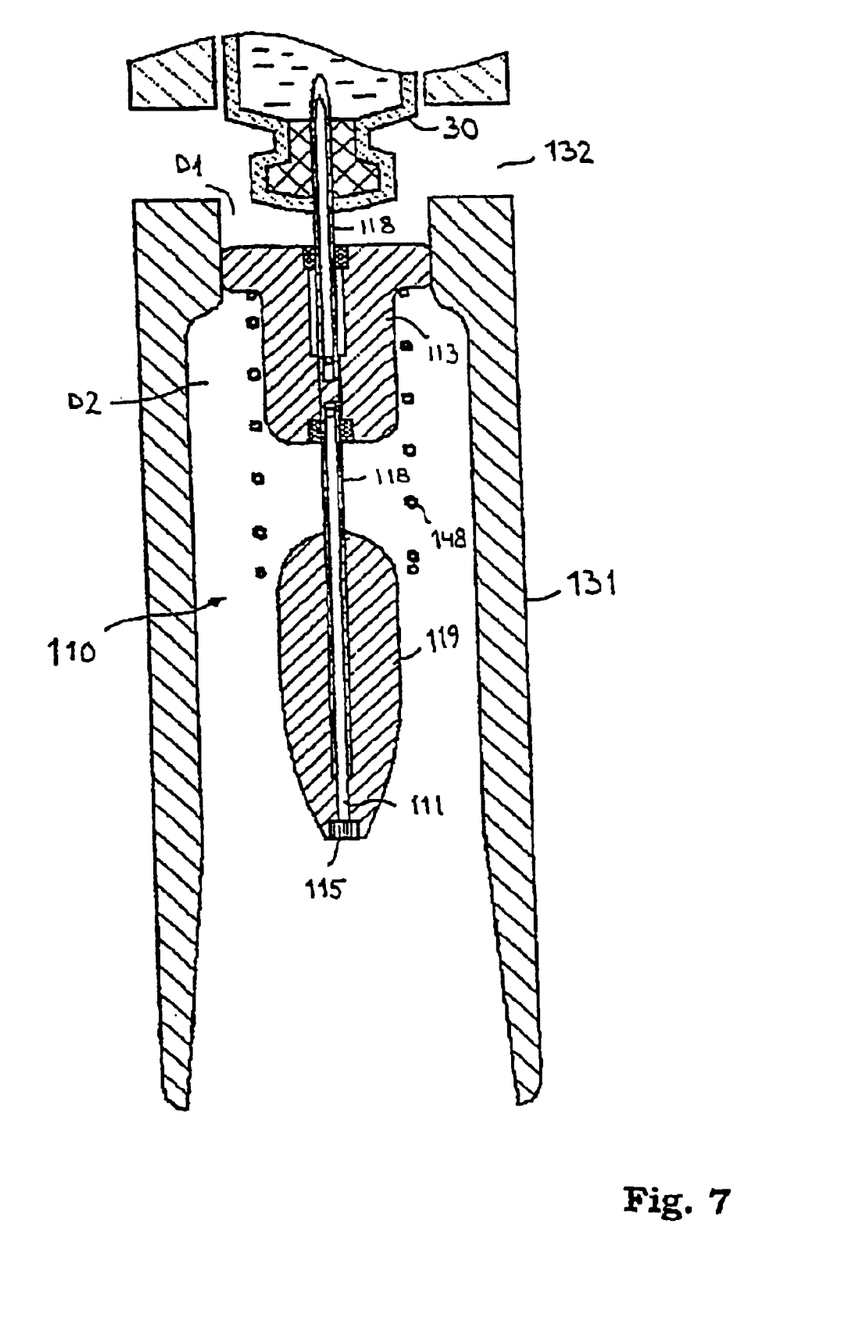
FIG. 7 is a cross sectional view through the mouthpiece of an inhalator with the aerosolizing unit according to FIG. 6.
Figure 8:
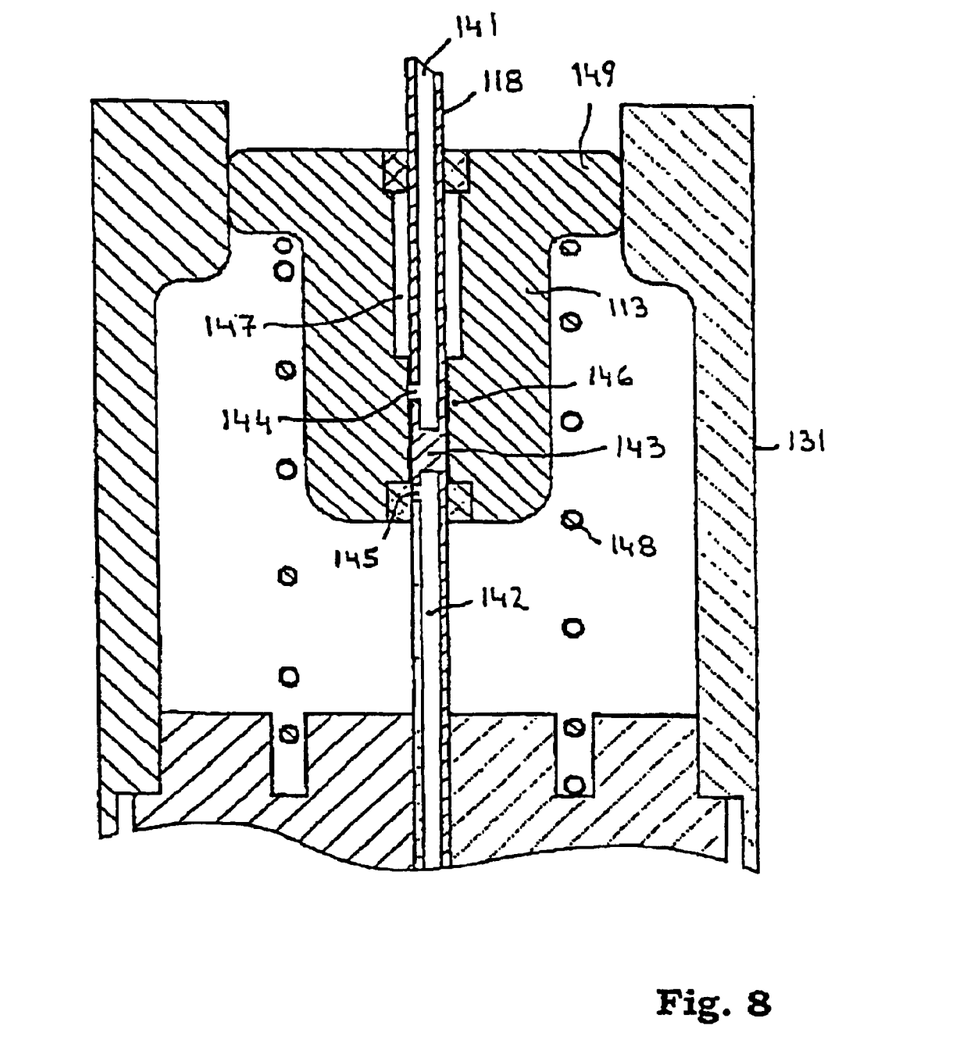
FIG. 8 is an enlarged cross sectional view through the mouthpiece and the upper part of the aerosolizing unit of FIG. 6, showing the aerosolizing unit in a first position wherein the drug administration is prevented.
Figure 9:
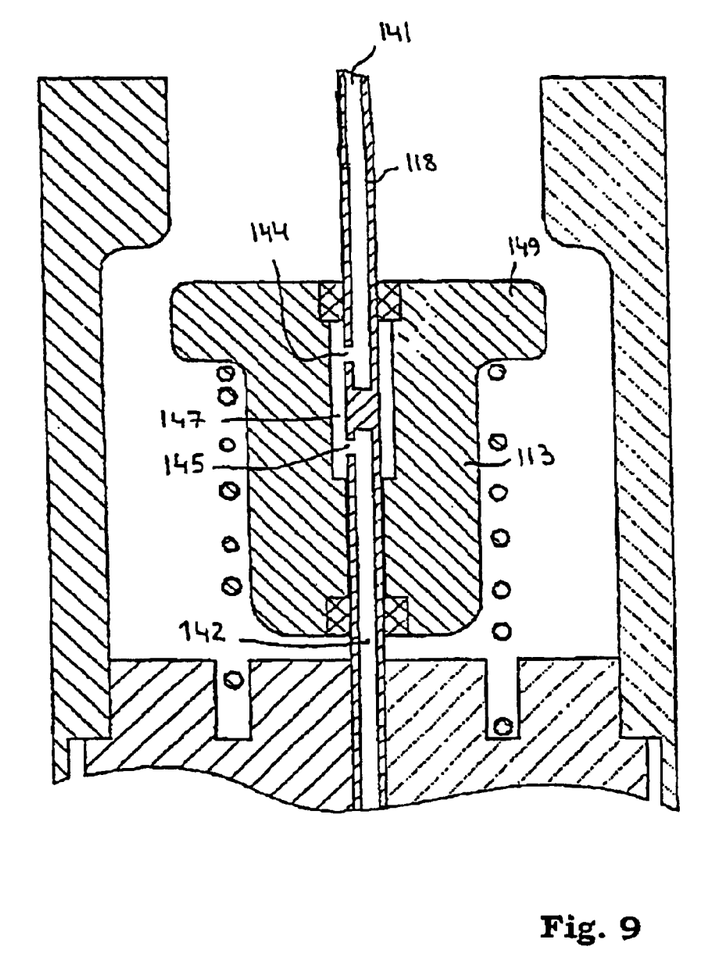
FIG. 9 is an enlarged cross sectional view corresponding to FIG. 8, showing the aerosolizing unit in a second position wherein the drug administration is allowed.

The aerosolizing unit 110 of FIG. 7 shall now be explained with reference to the cross sectional views of FIGS. 7, 8 and 9. Also, reference is made to the first embodiment as described above for the understanding of corresponding features.

The unit 110 is mounted within a mouthpiece 131 using the fastening means 122. The mouthpiece is hollow to provide a flow path for inhaled air. At its upper end the flow path exhibits a first section of a diameter D1, and downstream of the first section the flow path widens to a second diameter D2, i.e. D2>D1.

A drug cartridge 30 is mounted on the needle 118 to provide the drug to an inlet channel 141 extending through an upper section of the needle 118. The inlet channel 141 is parted from an outlet channel 142 of the needle by a barrier 143. A first opening 144 provides communication between the inlet channel 141 and the outside of the needle 118. Similarly, a second opening 145 provides communication between the outside of the needle 118 and the outlet channel 142.

The end of the outlet channel 142 of the needle 118 is in fluid communication with an atomizing device, such as a microporous membrane as described above, via a hollow section 111 of the unit 119.

A sleeve 113 is slidably threaded on the needle 118. A section 146 of the sleeve is adapted to provide a sealing over the first and second opening when the sleeve 113 is in a first position along the needle 118. Furthermore, an annular channel section 147 is provided in the sleeve 113, around the needle 118 and adjacent to the sealing section 146. Thus, in a first and sealing position with respect to the needle as shown in FIG. 8, the sealing section 146 of the sleeve 113 acts to prevent the pressurised liquid in the cartridge 33 to exit through the first opening 144. In a second position with respect to the needle 118 as shown in FIG. 9, the sleeve 113 acts to open communication between the inlet channel 141 and the outlet channel 142 of the needle 118, via the first opening 144, the channel section 147 and the second opening 145. Thus, the sleeve 113, and more specifically the sealing portion 146, forms a valve means for allowing and disrupting, respectively, a flow of drug to the aerosolizing means 115.

The sliding movement of the sleeve 113 is counteracted by a spring 148 that is inserted between the sleeve and the body 119. The initial resting position of the sleeve 113 corresponds to the first sealing position as described above.

The sleeve 113 is also provided with a flange portion 149 having a diameter to fit slidably within the first section of a diameter D1 in the mouthpiece 131.

Inlet openings 132 are provided in the inhalator casing to provide an air inlet during use.

During use, i.e. when the patient inhales through the proximal end of the mouthpiece 131, a pressure difference between the upper and lower side of the flange portion 149 will be obtained. When then pressure difference is sufficiently high, i.e. the patient inhales strong enough, the sleeve 113 will be urged downwards, and against the spring force of the spring 148, towards the body 119 of the aerosolizing unit 110 until the sleeve 113 has reached a second position within the part of the mouthpiece having an inner diameter of D2.

Thus, provided that the strength of the inhalation is strong enough to counteract the spring 148 (i.e. the flow rate of the air flow is above an opening flow rate), the sleeve 113 slides from its first sealing position to a second position wherein communication between the cartridge 30 and the aerosolizing means 115 is established. Therefore, as long as the sleeve 113 is in its second position aerosolized drug is discharged through the aerosolizing means 115 to be carried by the airflow into the air passages of the patient.

The force of the spring, as well as the dimension of the individual components of the aerosolizing unit, should be selected such that the inhalation needed to open the valve means 146 also ensures that an efficient drug inhalation is obtained.

The valve function of the sleeve 113 and its sealing portion 146 ensures that drug is delivered as long as the airflow through the mouthpiece is strong enough. When the airflow decreases below a certain limit, in the present embodiment approximately being the same as the opening airflow, the sleeve is urged back to its sealing position by the spring 148.

Thus, the sleeve 113, i.e. its sealing portion 146, not only forms a valve means but also, in cooperation with the mouthpiece and the spring 148, forms a valve actuating means.

The cartridge 30 is, in the second embodiment, biased by a piston and spring arrangement in correspondence with the description of the first embodiment.

FIGS. 10–13 show a third embodiment of an aerolizing unit where the same components as the previous embodiments have the same reference numbers. The aerolizing unit 200 is attached in the mouthpiece 31 of the inhaler in a suitable manner via a lower 202 and an upper 204 support piece. The support pieces are attached to each other by two fins or wings 206 extending radially from the longitudinal axis 208 of the aerolizing unit, FIG. 11. The lower support piece is arranged with a generally tubular, downwardly protruding holder 210. The end of the holder is arranged with a circumferential recess 212, in which a valve unit 214 is arranged. The valve unit comprises a circular lid 216 with a central opening 218 connecting to a passage arranged in an elongated tubular part 220 of the valve unit. Outside the opening a porous membrane 222, preferably a Rayleigh membrane is arranged. The passage has a first diameter and accommodates a metallic magnetically affectable ball 224, such as a steel ball. The passage then narrows to a lesser diameter, where the transition constitutes a seat for the ball. In the passage with lesser diameter, extending through the elongated part, a hollow needle 18 is inserted. The upper end of the needle is inserted in the cartridge 30 containing the liquid to aerolized. In all, this provides a communication from the interior of the cartridge to the membrane via the ball valve.

Figure 10:
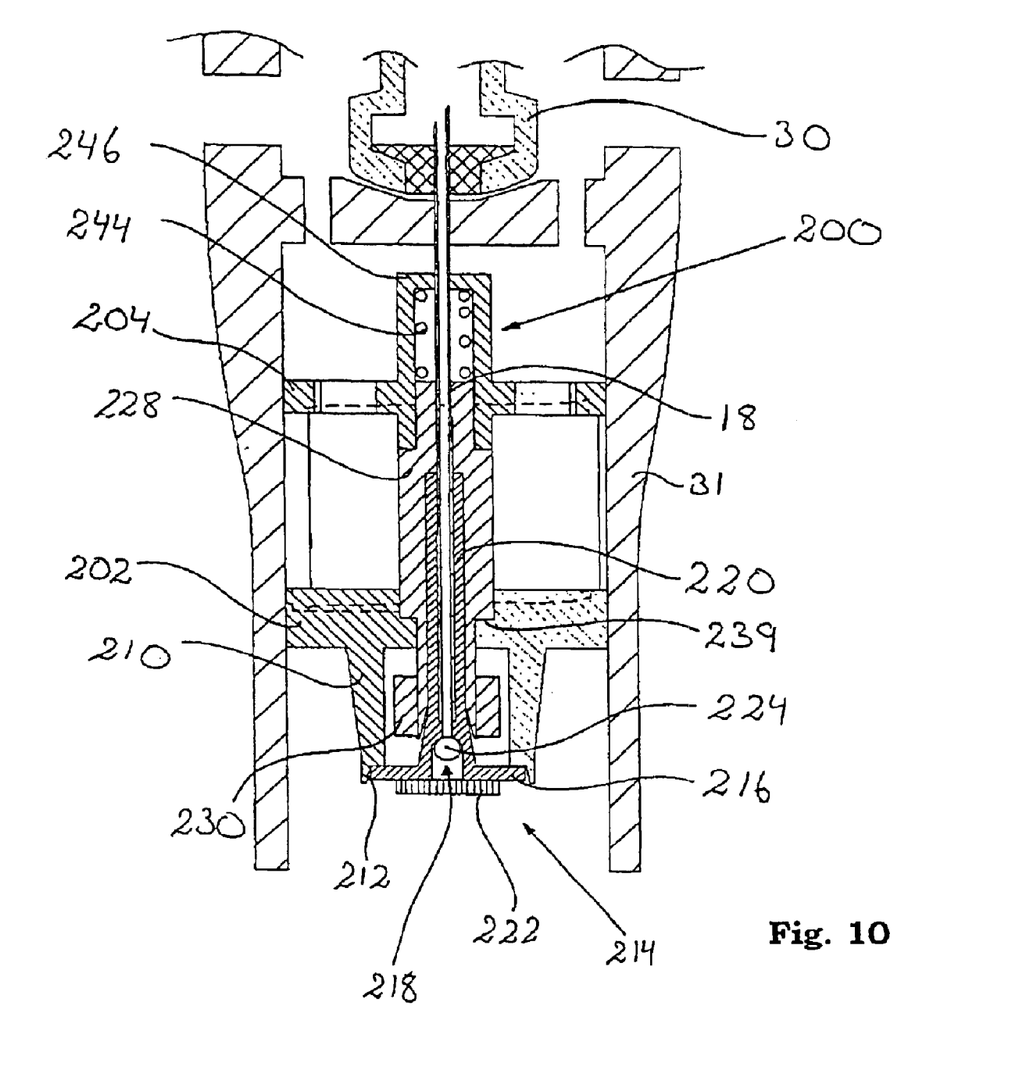
FIG. 10 is a cross sectional view through the mouthpiece and a third embodiment of an aerolizing unit according to the invention.

Outside the elongated tubular part and the needle, a generally tubular body 228 is rotatably arranged. The lower end of the tubular body extends through the lower support piece and terminates in the vicinity of the valve seat. The lower end is arranged with circumferential magnet 230. The lower support piece is arranged with arc-shaped air passages 232, FIG. 11. The tubular body is further arranged with two fins or sails 234 radially extending therefrom. The upper surface of the lower support piece and the lower surface of the upper support piece are arranged with sloping surfaces extending circumferentially. The lower support piece is arranged with two such surfaces 236, 238, one inside the air passage and one outside the air passage, where a lower ledge 239 of the tubular body 228 is resting on the inner surface 238.

The wings 234 may rest on the outer surface, but there may also be a certain gap between them, as will be explained below. The lower support piece is further provided with a stop ledge 240 for limiting the movement of the wings.

The upper support piece is arranged with two air passages 242, which are placed so that are arranged between a fixed and a movable wing, respectively, the function of which will be explained in detail below. A compression spring 244 is arranged in a housing 246 of the upper support piece and acts between this and an upper end of the tubular body.

The function is as follows. In rest position, the tubular body 228 with the movable wings 234 are positioned such by the influence of the compression spring 244 that the movable wings are in contact with the ledges 240 of the lower support piece. In that position, shown in FIG. 10, the magnet 230 is close to the valve seat and the ball 224, whereby the magnetic forces urge the ball upwards against the valve seat, thereby closing the passage. When a user inhales through the mouthpiece, an air flow is created through the air passages 242 of the upper support piece and between a fixed and a movable wing. This creates a pressure difference over the movable wings, which thereby urges the tubular body 228 to rotate around the needle 18 and the elongated part 220 of the valve unit against the force of the compression spring. The rotational movement causes the lower ledge 239 of the tubular body 228 to ride on the inner sloping surfaces 238 of the lower support piece 202, whereby the tubular body is moved upwards in FIG. 10. Since the tubular body is lifted, so is also the magnet, whereby the distance between the magnet and the ball increases. This in turn decreases the magnetic force on the ball. At a certain distance between them, the pressure on the liquid from the cartridge 30 exceeds the magnetic force, whereby the valve opens. The pressurized liquid is then forced through the membrane, thereby aerolising the liquid. When the user terminates the inhalation, the force from the compression spring pushes the tubular body against the sloping surfaces, whereby the tubular body is rotated back to its initial position, which also lowers it. The lowering of the tubular body 228 brings the magnet 230 closer to the ball 224 until the magnetic forces exceeds the pressure form the liquid, and the valve closes. Of course, if the whole dose of pressurized liquid is emptied during the inhalation, the magnetic forces only have to exceed any eventual gravitational forces.

Figure 11:
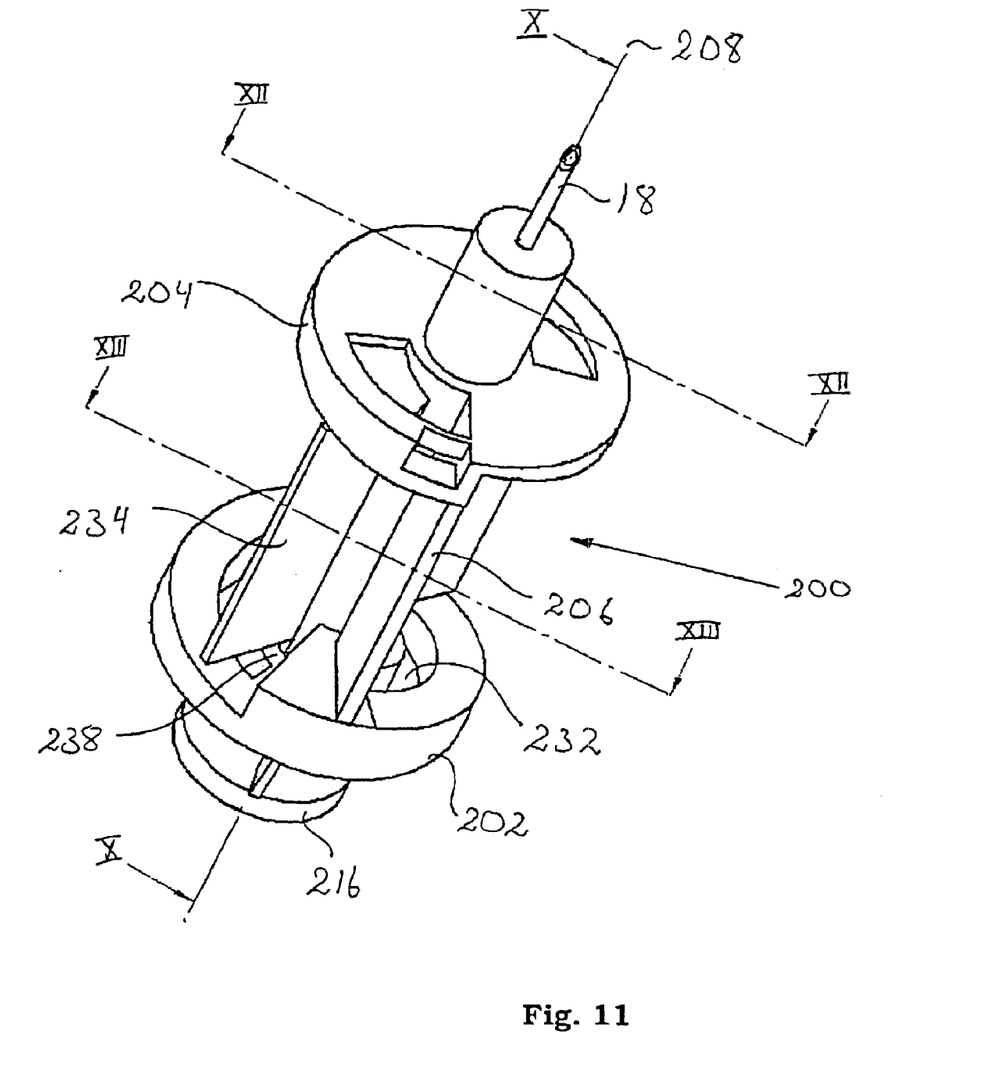
FIG. 11 is a perspective view of the aerolizing unit of FIG. 10.
Figure 12:
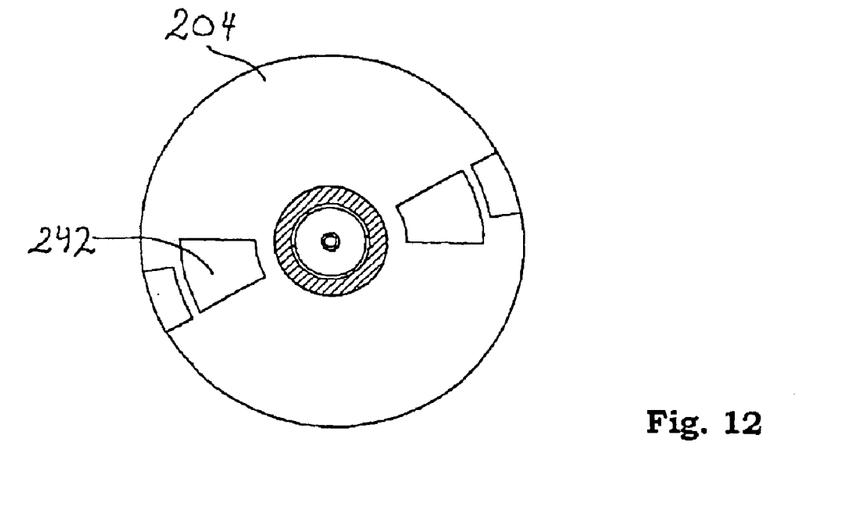
FIG. 12 is cross sectional view taken along line XII—XII of FIG. 11.
Figure 13:
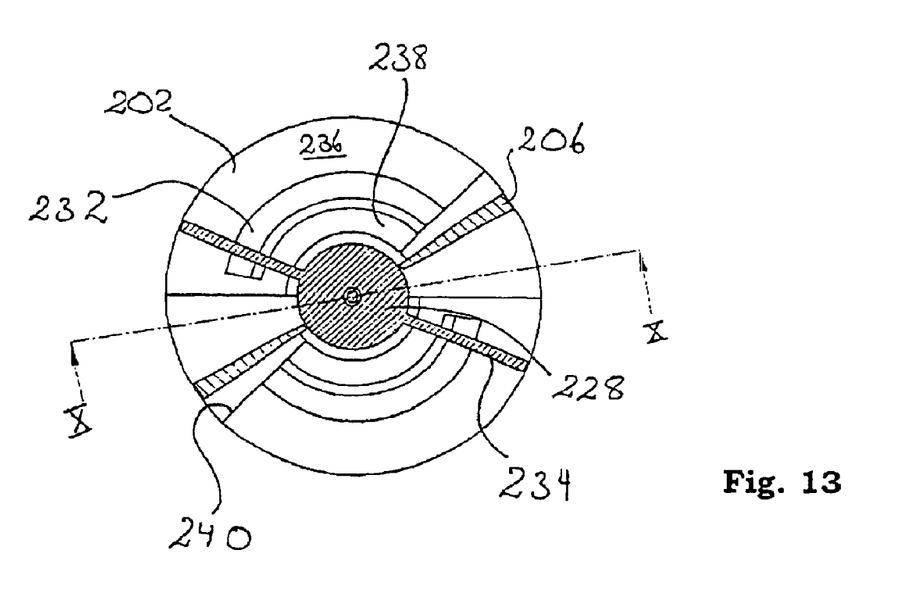
FIG. 13 is cross sectional view taken along line XII—XII of FIG. 11.
Figure 14:
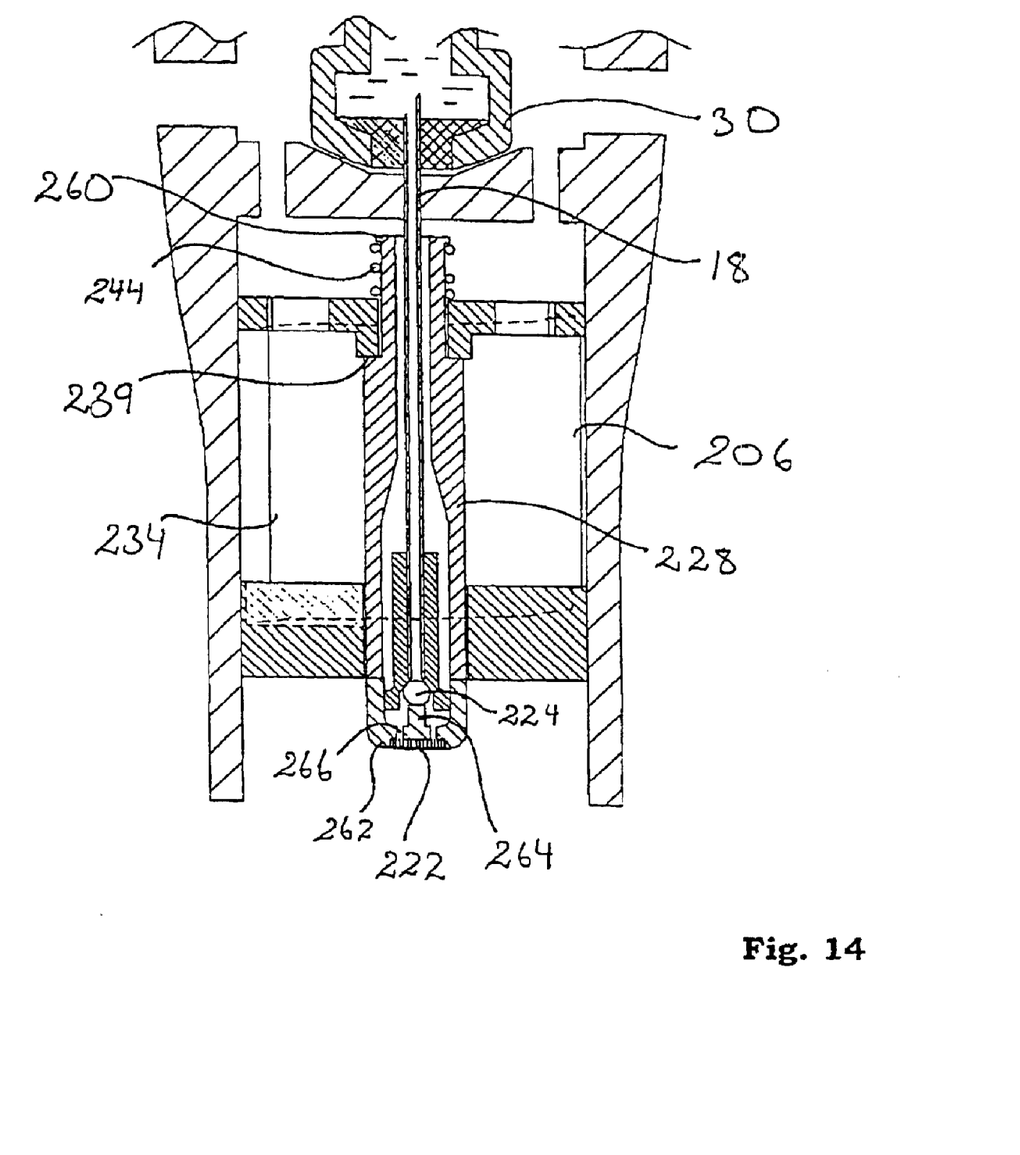
FIG. 14 is a cross sectional view of the mouthpiece and a variant of the aerolizing unit of FIG. 10.

FIG. 14 shows a variant of the embodiment of FIG. 11. It also comprises two fixed wigs 206 attached to the upper and lower support pieces and two movable wigs 234 attached to a movable tubular body 228. However, in this case the lower surface of the upper support piece is arranged with sloping surfaces on which the tubular body 228 rests with an upper ledge 239, urged by a compression spring 244 acting between a ledge 260 on the tubular body and the upper support surface, which compression spring urges the tubular body and compression spring upwards in FIG. 14.

A hollow needle 18 is inserted into the cartridge 30 and fixedly attached to the housing of the inhaler. The lower part of the needle is arranged with an elongated tubular member 220, the lower end of which has a somewhat larger diameter, where the transition constitiutes a valve seat. A ball 224 is arranged to the valve seat. The tubular body 228 extends below the lower end of the tubular member 220 and encloses it with an end wall 262. The inwardly surface of the end wall is arranged with a support projection 264, which, when the tubular body is in the rest position, pushes the ball against the valve seat. The end wall is further provided with a number of passages 266, which are in fluid connection with a porous membrane 222, such as a Raileygh membrane.

The function of this variant is as follows. As described above, the compression spring 244 urges the tubular body 228 upwards and in its resting position, the tubular body 228 is resting against the ledges of the upper support piece in this case. The ball 224 is now pressed against the valve seat and the valve is closed. When a user inhales, the pressure difference over the movable wings, as described above, causes the tubular body 228 to rotate against the force of the compression spring. Because the tubular body rests against the sloping surfaces of the upper support piece, the tubular body with its end wall and support projection 264 is lowered in respect to the needle and the tubular member. The lowering of the support projection causes the ball to be free from the valve seat thereby permitting the pressurized liquid from the cartridge to flow past the valve, through the passages 266 and through the membrane 222, thereby aerolizing the liquid.

When the user terminates inhalation, the force from the compression spring urges the tubular body upwards, and because it is resting on the sloping surfaces, the tubular body will be lifted. The support projection is also lifted and pushes the ball against the valve seat, thereby closing the valve.

Even though a ball has been shown and described in the last two embodiments, it is to be understood that other movable bodies capable of forming a valve unit together with a valve seat are may be employed, such as for example conically shaped bodies. As for the embodiment according to FIG. 10, the movable body may also be manufactured of a magnetic material in order to increase the force between the magnet and the movable body. Preferably the movable body then has a form that ensures a certain orientation so that the magnets cooperate.

The aerolising units shown in the drawings 10–14 are only to be regarded as illustrative examples. The actual units used may have different dimensions depending on the demands and space available of an inhaler. As regards for example an anti-smoking inhaler, the inhaler body should be long and rather thin, whereby the aerolising unit has to be adapted accordingly. As regards the inclination of the sloping surfaces the size and placement of the air passages, spring characteristics and the like components affecting the function, these may be altered in many ways in order to optimizing the performance of the device depending the application, the users breathing abilities and such.

Thus, with an inhalator and an aerosolizing unit according to the invention, a drug is administered to a patient in an aerosolized form using a portable handheld device.

The drug is delivered continuously as long as the patient inhales with a strength selected to ensure a good inhalation effect.

Except for the force needed for biasing the pressure in the liquid during the assembly of the inhalator the only power needed to actuate the valve means is the force developed by the breath of the user. Thus, the user does not need to rely on a separate power source, such as a battery. Of course, embodiments wherein the biasing is performed as a separate step could be possible as well.

A mechanical inhalator, such as an inhalator according to the embodiments shown, has remarkably few and simple components, and is therefore relatively cheap and easy to manufacture, even in handheld sizes.

The all mechanical inhalator, as regards administering the drug, is reliable in that the user does not have to worry about the freshness or availability of batteries or any additional sources of energy.

A preferred use of the aerosolizing unit according to the invention is within the field of antismoking treatment. Within this field it is known to treat the patient with nicotine. It has been found that it is advantageous to provide the nicotine to the patient in a way that is as similar to smoking as possible.

The aerosolizing unit of the present invention is well suited for such a use, since a small amount of the pharmaceutics is delivered each time the user inhales with a breath strong enough. Also, the inhalator could be designed to resemble the size and shape of a cigarette, as is shown in FIG. 3.

However, in the embodiments of an inhalator as described above, nothing prevents the user from continue to inhale pharmaceutics by successive inhalations until the container is emptied.

Unless the container holds one dosage unit only, this implies a risk for overdosing. Also, if a replaceable container holds one dosage only, the need to change the pharmaceutics container for each treatment might be perceived as uncomfortable and disturbing.

Therefore, it is preferred to provide the pharmaceutics in a multi-dose container. This calls for a dosage mechanism that prevents the user from unintentionally receiving more that one unit dose.

Two embodiments of such dosage mechanism shall now be described.

A first embodiment of such a dosage mechanism comprises a dose unit compartment between the cartridge and the valve mechanism (such as the valve provided by the member 13 of the first embodiment above, or the sleeve 113 of the second embodiment) of the aerosolizing unit. An additional valve is provided between the cartridge and the unit dose compartment. Before inhalation the patient opens the additional valve to fill the unit dose compartment with a unit dose of the drug, and then shuts the valve. Thus, pressurised liquid of one unit dose is contained in the compartment, and is aerosolized according to the description above when the user inhales trough the inhalator. To receive a next dose, the patient has to repeat the loading of the unit dose compartment. Such a dose unit compartment and additional valve may of course be included in the embodiments according to FIGS. 10–14, even though they are not indicated in these.

A second embodiment of a dosage mechanism utilizes the axial movement of the piston in the inhalator upper section, used to pressurise and discharge liquid from the cartridge into the aerosolizing unit. A simple latch mechanism, wherein a releasable latch is in engagement with recesses in the piston. The recesses are spaced apart along the piston, spaced from each other with a distance corresponding to the piston stroke needed to displace one unit dose. Thus, the latch mechanism allows the piston to move only a distance corresponding to one unit dose. When such a unit dose has been inhaled, the patient has to manipulate the latch to activate the next dose.

With a dosage mechanism as described above, the user sets the dosage mechanism to permit the next unit dose, and may puff, i.e. inhale with small inhalations, until the predetermined dose is received. Actually, it is possible to adapt the dosage mechanism to a variable dose setting by using a screw mechanism similar to an insulin injector.

Although the use of the inhalator for introducing a pharmaceutically active substance into a human body has been described above, it is of course possible to use the inhalator for other purposes as well, such as to refresh the breath or to introduce a generally well tasting substance into the mouth.

Similarly, the inhalator could be adapted for inhalation through the nose as well as through the mouth.

It is obvious that the present invention may be varied in many ways with respect to the detailed description above. Such variations are not to be regarded as a departure from the spirit and scope of the invention, and all such modifications as would be obvious to one skilled in the art are intended to be included within the scope of the following claims.

What is claimed is:

1. A portable, handheld breath actuated inhalator, to aerosolize and distribute a pressurised liquid, including, arranged in a housing,
   a breath flow path defined between an air inlet and a mouthpiece outlet,
   a container containing the liquid to be distributed,
   mechanical pressurizing means for constantly applying a pressure on the liquid in said container,
   a liquid conduit in flow communication with an interior of said container,
   an aerosolizing membrane with through pores of microscopic size in said breath flow path and in flow communication with said liquid conduit, said aerosolizing membrane aerosolizing the pressurized liquid and introducing the aerosolized liquid into the breath flow path,
   a mechanical valve means between said container and said aerosolizing membrane for controlling fluid communication between said container and said aerosolizing membrane, thereby controlling the introduction of the aerosolized liquid into the breath flow path, and
   a mechanical actuating means in said breath flow path, said mechanical actuating means for opening said mechanical valve means when a first level of an inhalation flow parameter in said breath flow path is reached and for closing said mechanical valve means when a second level of the inhalation flow parameter is reached.

2. The inhalator according to claim 1, wherein said valve comprises a sleeve (113) surrounding a tubular conduit (118) for slidable, sealing movement along said conduit (118), said conduit having a first section (141) in fluid communication with the container (30) of the liquid, and said first section (141) having an outlet opening (144), and a second section (142), separate from said first section (141), in fluid communication with the aerosolizing membrane (115) and said second section (142) having an inlet opening (145),
   wherein said sleeve (113) includes a channel (147) and a sealing section (146) arranged such that said sealing section (146) in a first position of said sleeve (113) seals said outlet (144) and inlet (145) openings, respectively, and in a second position of said sleeve (113) communication is opened between said outlet opening (144) and said inlet opening (145) via said channel (147);
   and wherein said mechanical actuating means comprises a flange member (149) connected to said sleeve for moving therewith, said flange member (149) being arranged in the breath flow path to be movable by the action of the air flow to move the sleeve from said first position to said second position, and a spring means (148) for returning said sleeve to said first position.

3. The inhalator according to claim 1, wherein said inhalation flow parameter is selected from the group consisting of the inhalation flow rate and the inhalation air pressure within the breath flow path.

4. The inhalator according to claim 1, wherein the first level of inhalation flow parameter is substantially the same as the second level of inhalation flow parameter.

5. The inhalator according to claim 1, wherein the first level of inhalation flow parameter substantially differs from the second level of inhalation flow parameter.

6. The inhalator according to claim 1, wherein said valve (214) comprises a movable body (224) arranged in a passage (218), which passage is in fluid communication with the liquid container (30), the passage having a seat and the movable body and the seat having corresponding shapes as to form a sealing connection,
   said mechanical actuating means comprises a body (228) rotationally arranged in said inhalator, the body comprises means (230, 262, 264) for urging said movable body against said seat, air flow directing means (206, 232, 234, 242) arranged to said body and said inhaler, arranged and designed such that, upon inhalation, a pressure difference is created over the flow directing means of said body (234), which pressure difference causes said body to rotate, thereby moving said urging means away from said movable body, and opening said valve means.

7. The inhalator according to claim 6, wherein the movable body of the valve comprises a magnetically affected material, and that said urging means comprises a magnet (230).

8. The inhalator according to claim 7, further comprising cam-shaped surfaces on which the rotationally arranged body rests, which cam-shaped surfaces transform the rotational movement of the body to a linear movement.

9. The inhalator according to claim 7, further comprising spring means (244) for urging the rotationally arranged body to its initial position after end of inhalation.

10. The inhalator according to claim 6, wherein said urging means comprises a holding member attached to said body and in contact with said movable body.

11. A breath actuated inhalator for aerosolizing and distributing a pressurised liquid, comprising:

- a breath flow path defined between an air inlet and a mouthpiece outlet;
- a container for the liquid;
- an aerosolizing membrane for aerosolizing the liquid and introducing the aerosolized liquid into said breath flow path;
- a valve controlling the introduction of the aerosolized liquid into said breath flow path, said valve being between said container and said aerosolizing membrane and allowing fluid communication between said container and said aerosolizing membrane;
- a mechanical actuator regulating said valve and being energized by a flow of inhaled air;
- wherein the valve means is a moveable sealing member for closing a conduit in communication with said container and comprising a first magnetic member and wherein said mechanical actuating actuator comprises a flexible membrane moveable in response to an air pressure created by the flow of inhaled air and a second magnetic member connected to said flexible membrane for moving therewith,
- wherein said first and the second magnetic members are arranged in a repelling relationship to each other for urging said sealing member to close said conduit.

* * * * *